US 6,677,271 B1

(12) United States Patent
Birke et al.

(10) Patent No.: US 6,677,271 B1
(45) Date of Patent: Jan. 13, 2004

(54) NICKEL CATALYST FOR HYDROGENATING FUNCTIONAL GROUPS AND METHOD FOR PRODUCING SAME

(75) Inventors: Peter Birke, Langenbogen (DE); Reinhard Geyer, Halle (DE); Peter Kraak, Leipzig (DE); Rainer Schodel, Teutschenthal (DE)

(73) Assignee: Kataleuna GmbH Catalysts (DE)

( * ) Notice: Subject to any disclaimer, the term of this patent is extended or adjusted under 35 U.S.C. 154(b) by 0 days.

(21) Appl. No.: 09/914,556

(22) PCT Filed: Mar. 1, 2000

(86) PCT No.: PCT/EP00/01708

§ 371 (c)(1),
(2), (4) Date: Nov. 30, 2001

(87) PCT Pub. No.: WO00/51727

PCT Pub. Date: Sep. 8, 2000

(30) Foreign Application Priority Data

Mar. 3, 1999 (DE) .......................................... 199 09 177

(51) Int. Cl.[7] .............................................. B01J 23/755
(52) U.S. Cl. ...................................... 502/337; 502/349
(58) Field of Search ................................ 502/242, 259, 502/337, 349

(56) References Cited

U.S. PATENT DOCUMENTS

| | | | |
|---|---|---|---|
| 2,564,331 A | 8/1951 | Hawley | ........................ 252/472 |
| 3,868,332 A | 2/1975 | Carter et al. | |
| 3,988,262 A | 10/1976 | Anderson et al. | |
| 4,002,658 A | * 1/1977 | Dalla Betta et al. | ........ 518/705 |
| 4,090,980 A | * 5/1978 | Carter et al. | ................. 502/245 |
| 4,160,745 A | * 7/1979 | Murrell et al. | ............... 502/185 |
| 4,634,515 A | * 1/1987 | Bailey et al. | .................. 208/91 |
| 4,668,654 A | 5/1987 | Drake | |
| 4,670,416 A | * 6/1987 | Klimmek et al. | ............ 502/259 |
| 4,694,113 A | 9/1987 | Gauthier et al. | ............. 568/863 |
| 4,956,328 A | 9/1990 | Frohning et al. | |

FOREIGN PATENT DOCUMENTS

| | | |
|---|---|---|
| DD | 156175 | 8/1982 |
| DD | 217996 | 1/1985 |
| DE | 1257753 | 1/1968 |
| DE | 3537247 | 4/1987 |
| DE | 3811038 A1 | 10/1989 |
| EP | 0089762 | 9/1983 |
| EP | 0098681 | 1/1984 |
| EP | 0335222 | 3/1988 |
| EP | 057662 A | 5/1994 |
| EP | 0672452 | 9/1995 |
| EP | 0672452 A1 | 9/1995 |
| JP | 55-13333 | 1/1980 |
| NL | 8102190 | 5/1981 |
| SU | 283185 | 12/1970 |
| SU | 565040 | 8/1977 |

* cited by examiner

Primary Examiner—Tom Dunn
Assistant Examiner—Christina Ildebrando
(74) Attorney, Agent, or Firm—Ostrolenk, Faber, Gerb & Soffen, LLP

(57) ABSTRACT

The invention relates to a catalyst, in particular for the hydrogenation of functional groups of organic compounds in the presence of water, comprising nickel on a support, the catalyst being reduced and stabilized.

20 Claims, No Drawings

NICKEL CATALYST FOR HYDROGENATING FUNCTIONAL GROUPS AND METHOD FOR PRODUCING SAME

DESCRIPTION

The invention relates to a catalyst which can be employed for the hydrogenation of functional groups of organic compounds in the presence of water, in particular for the hydrogenation of nitro groups in nitroaromatics to give the corresponding amines in the presence of water or for the hydrogenation of aldoses and ketoses to the corresponding sugar alcohols in the presence of water, and to a process for its preparation.

The industrially most frequent applications of the hydrogenation of functional groups of organic compounds are the hydrogenation of aldoses or ketoses to the corresponding sugar alcohols or of nitroaromatics to the corresponding amines.

The hydrogenations are in general carried out either in a fixed-bed reactor or in a batch reactor. On the industrial scale, hydrogenations are most frequently performed in the liquid phase using a suspended catalyst, the processes differing by the reaction temperature, the pressure, the catalyst, the solvents and the nature of the reaction procedure. Catalysts used here are various catalyst systems, such as, for example, nickel-containing catalysts. The catalytic hydrogenation of glucose to sorbitol using a nickel-$SiO_2$—$Al_2O_3$ catalyst is disclosed in NL 8 102 190. The use of nickel-copper supported catalysts for the hydrogenation of glucose is disclosed in DD 217 996. Supports used are $SiO_2$, $Al_2O_3$ and $SiO_2 \cdot Al_2O_3$. In DD 156 175, the obtainment of sorbitol by hydrogenation of glucose in the presence of an Ni—$SiO_2$ catalyst is described. According to patent specification SU 565 040, hydrogenation to sorbitol on Raney nickel catalysts at a catalyst concentration of 5 to 6%, temperatures of 110 to 150° C. and pressures of 40 to 60 bar proceeds with obtainment of good yields after 1 to 2 hours. U.S. Pat. No. 4,694,113 describes a two-stage process for the hydrogenation of glucose to sorbitol, approximately 95% of the glucose being hydrogenated in the presence of a nickel catalyst to give sorbitol in the first stage and, after removal of the nickel catalyst, the remainder of the glucose being hydrogenated to sorbitol using an Ru catalyst.

JP 551 33 33 discloses the hydrogenation of 2,4-dinitrotoluene and 2,6-dinitrotoluene in the presence of the catalysts Pd/C, Raney nickel, Raney cobalt or platinum black.

EP-A 98 681 discloses a nickel-kieselguhr supported catalyst for the hydrogenation of dinitrobenzophenone to the corresponding diamine.

In DE-A 35 37 247, the hydrogenation of dinitro compounds to the diamines in the presence of modified Raney nickel catalysts is described.

EP-A 0 335 222 discloses the use of nickel-$Al_2O_3$/$ZrO_2$ supported catalysts for the hydrogenation of nitrites, aromatics, nitro compounds and olefins. The specification discloses, inter alia, the simultaneous precipitation of nickel, zirconium and aluminum on supports at 50 to 120° C. and at a pH of 7.3 to 9.0, the supports employed being active carbon, $Al_2O_3$, $SiO_2$, kieselguhr and others.

SU patent 28 31 85 discloses nickel-$Al_2O_3$/$ZrO_2$ catalysts which were prepared by precipitating nickel and $Al_2O_3$ on $ZrO_2$.

According to the teaching of U.S. Pat. No. 2,564,331, a nickel-$ZrO_2$ catalyst is prepared by precipitating a nickel and zirconyl carbonate mixture with subsequent washing, drying and reduction at 250 to 350° C., the catalyst containing at most 10 mass % of $ZrO_2$.

The precipitation of insoluble carbonates is also disclosed in DE-B 1 257 753, the precipitation process being induced by evaporation of $CO_2$ and $NH_3$ from a mixed salt solution of ammonium zirconyl carbonate and nickel ammine carbonate.

EP-A 0 672 452 discloses catalysts for the hydrogenation of organic compounds, which essentially contain 65 to 80 mass % of nickel, calculated as NiO, 10 to 25 mass % of $SiO_2$, 2 to 10 mass % of zirconium, calculated as $ZrO_2$ and 0 to 10 mass % of aluminum, calculated as $Al_2O_3$, the sum of the content of $SiO_2$ and $Al_2O_3$ being at least 15 mass %. These catalysts are prepared by addition of an acidic aqueous solution of Ni, Zr and, if desired, aluminum compounds to a basic aqueous solution or suspension of silicon compounds and, if desired, aluminum compounds. During the precipitation, the pH is first lowered to 4.0 to 6.5 and subsequently adjusted to 7 to 8. The precipitation product is dried, calcined and shaped.

The previously known nickel hydrogenation catalysts all have the disadvantage that under the hydrothermal reaction conditions both of the hydrogenation of glucose and of nitroaromatics a rapid aging of the catalysts occurs.

The technical problem underlying the present invention is thus to make available nickel-containing supported catalysts which, in particular under the hydrothermal reaction conditions of the hydrogenation of glucose and nitroaromatics, have a higher lifespan than the conventional catalysts.

This problem is achieved according to the invention by making available a catalyst, in particular for the hydrogenation of functional groups of organic compounds, in particular for the hydrogenation of glucose to sorbitol or of nitro groups in nitroaromatics to the corresponding amines in the presence of water, comprising nickel on a support, the catalyst being reduced and stabilized, contains nickel crystallites having a monomodal nickel crystallite size distribution, a nickel content of 25 to 60 mass % (based on the total mass of the catalyst), in particular 25 to 59 mass % (based on the total mass of the catalyst) and a degree of reduction of at least 65%. The degree of reduction is determined after a one-hour afterreduction of the stabilized catalyst at 100° C. in a stream of hydrogen (loading: 1 000 v/vh).

The invention solves this problem also by the making available of a process for the preparation of such a catalyst.

The invention provides in a particularly preferred embodiment that the above-mentioned catalyst has a monomodal nickel crystallite size distribution, the maximum of the nickel crystallite size distribution being 25 to 90 angstroms, in particular 30 to 90 angstroms.

In a further preferred embodiment, it is provided that the above-mentioned catalyst is supported on a zirconium-containing support, preferably contains $ZrO_2$, $ZrO_2HfO_2$, $SiO_2 \cdot ZrO_2$, $SiO_2 \cdot ZrO_2HfO_2$ or mixtures of at least two substances thereof or consists of these.

In a particularly preferred embodiment, the $SiO_2$ content is 0 to 40 mass % (based on the total mass of the catalyst). In a further preferred embodiment, the $ZrO_2$ content is 20 to 75 mass % (based on the total mass of the catalyst). In a further preferred embodiment, the $HfO_2$ content is 0 to 7.5 mass % (based on the total mass of the catalyst).

In a particularly preferred embodiment of the invention, the reduced and stabilized catalysts can be employed as powders having particle sizes of 1 to 100 μm, preferably of 2 to 30 μm. Of course, shaped articles can also be employed.

The catalysts according to the invention are distinguished in an advantageous and surprising manner by their prolonged lifespan with identical or improved catalytic activity compared with conventional catalysts. Catalysts of the monomodal nickel crystallite size distribution according to the invention have, in particular under hydrothermal reaction conditions, a considerably prolonged lifespan compared with conventional catalysts.

In connection with the present invention, a monomodal nickel crystallite size distribution is understood as meaning a distribution of the nickel crystallites according to which only a maximum of the crystallite size distribution is present.

In connection with the present invention, the term degree of reduction is understood as meaning the proportion of the metallic nickel in the total nickel content of the stabilized catalyst which is present after a one-hour afterreduction at 100° C.

The invention also relates in a further embodiment to a process for the preparation of the above-mentioned catalyst. The invention thus also relates to a process for the preparation of a nickel-containing supported catalyst, in particular of a catalyst for the hydrogenation of carbonyl groups in aldoses or ketoses in the presence of water and of nitro groups in nitroaromatics to the corresponding amines in the presence of water, where, by precipitation from an $Ni^{2+}$- and $Zr^{4+}$-containing solution with a basic solution, in particular a solution of $NaOH$, $NaHCO_3$ or $Na_2CO_3$ or a mixture of at least two of these substances, up to a pH of 8 to 9 a precipitation product is obtained which is calcined at temperatures from 300° C. to 650° C., optionally then inertized, and subsequently reduced with hydrogen at temperatures from 250° C. to 550° C., in particular 300° C. to 550° C., optionally inertized, and subsequently stabilized.

In a particularly preferred embodiment, the $Ni^{2+}$- and $Zr^{4+}$-containing solution additionally contains $Hf^{4+}$. In a further preferred embodiment, the $Ni^{2+}$ and $Zr^{2+}$-containing solution or the $Ni^{2+}$ and $Zr^{4+}/Hf^{4+}$-containing solution contains silica $SiO_2$, preferably in suspended form. In a preferred embodiment it can be provided that the $Ni^{2+}$- and $Zr^{4+}$-containing solution contains nitrates, in particular in the form of zirconyl nitrate.

The precipitation product is thus prepared by addition of the basic solution mentioned to the $Ni^{2+}$- and $Zr^{4+}$-containing solution, this addition being carried out until the mixture of the two solutions reaches a final pH of 8 to 9.

The invention provides in a preferred embodiment that the precipitation takes place at temperatures from 60° C. to 95° C. In the preferred embodiment, it can be provided that, after the precipitation has been carried out, i.e. the final pH has been reached, the suspension obtained is subsequently stirred, for example, for one to two hours before further processing.

In a further embodiment, the invention relates to an aforementioned process, the precipitation product being filtered after the precipitation, washed, preferably with water, and subsequently dried at temperatures from 110° C. to 150° C. in a nonreducing atmosphere and a precursor catalyst being obtained.

In connection with the present invention, a precursor catalyst is understood as meaning a product which is obtained after the precipitation of the starting components, i.e. of the $Ni^{2+}$- and $Zr^{4+}$-containing, optionally $Hf^{4+}$-containing solution, and optionally of the $SiO_2$ with the basic solution added, filtration, washing with water and drying at temperatures in a nonreducing atmosphere.

According to the invention, in the preparation of the precursor catalyst phases of nickel hydroxynitrate ($Ni_3(OH)_4(NO_3)_2$) or nickel hydroxynitrate ($Ni_3(OH)_4(NO_3)_3$-containing phases, in particular mixtures of nickel hydroxynitrate ($Ni_3(OH)_4(NO_3)_2$), nickel hydroxycarbonate ($Ni_2(OH)_2CO_3 \cdot 4H_2O$) and nickel hydroxysilicate ($Ni_3Si_2O_3(OH)_4$) or mixtures of nickel hydroxynitrate ($Ni_3(OH)_4(NO_3)_2$) and nickel hydroxide ($Ni(OH)_2$) result having lattice widenings or a sepiolite-like structure ($Ni_4Zr_6O_{15}(OH)_2$), where $OH^-$ ions can be partially replaced by carbonate ions.

In connection with the present invention, lattice widening is understood as meaning a shift in the interference position to smaller angles.

Either before or after the calcination, the catalyst precursor can be shaped to give tablets, extrudates, cushion-like articles, spheres or the like.

The reduction of the calcined product can be carried out according to the invention both on the powder and on the shaped articles. According to the invention, it is particularly preferred to employ gas loadings in the range from 500 to 3 000 v/v h during the reduction.

According to the invention, it is provided in a preferred embodiment that the catalysts are stabilized after the reduction, preferably using an $O_2$—$N_2$—$CO_2$ mixture.

The invention therefore also relates to the making available of a process for the passivation of a preferably reduced and/or preferably inertized catalyst according to the invention, the catalyst being treated in a process step a) in a $CO_2$—$N_2$ gas mixture having a $CO_2$ content of 0.5 to 10% by vol. at temperatures from 91° C. to 350° C. for at least 30 minutes, in a process step b) subsequently being cooled in the gas mixture mentioned in step a) to a temperature of at most 90° C., then in a process step c) after reaching the temperature of at most 90° C. being added in a first passivation phase to the gas mixture oxygen, preferably air, up to a content of 0.2 to 1.5% by vol. of oxygen and the catalyst being treated in the mixture for at least 30 minutes with shaking and then in a process step d) the $CO_2$ content in the gas mixture according to step c) being reduced in a second passivation phase to <0.1% by vol. and the $O_2$ content being increased to 1.5 to 21% by vol.

The procedure according to the invention for the stabilization of the catalyst has the advantage of short stabilization times, at the same time readily reactivatable catalysts having very good thermal stability being obtained. In an advantageous manner, the catalysts are particularly uniformly passivated. Indeed, it was surprising that by the treatment with $CO_2$-low inert gases under the conditions indicated, very uniform and readily reactivatable catalysts were obtained.

The invention relates in a preferred embodiment to an aforementioned process, at least the passivation being carried out continuously or in a batch process in a catalyst bed, in particular using a catalyst bed whose height to diameter ratio is in the range from 0.05 to 1.

In a further preferred embodiment, the invention provides an aforementioned process, the concentration of the $CO_2$ during the treatment with the $CO_2$—$N_2$ mixture according to process step a) being 1 to 2.5% by vol.

In a further preferred embodiment, the invention provides an aforementioned process, the gas loading during the treatment with the $CO_2$—$N_2$ mixture according to process step a) being 500 to 10 000 v/v h. In a further preferred embodiment, the invention proposes that the aforementioned process, a gas loading during the treatment with the $CO_2$—$N_2$ mixture according to process step a) and/or during the treatment with the $CO_2$—$N_2$—$O_2$ gas mixture according to process steps c) and d) is 100 to 3 000 v/v h.

The invention provides in a further preferred embodiment that the aforementioned process, the treatment in the $CO_2$—$N_2$—$O_2$ gas mixture according to process steps c) and d), is carried out for a period of time of 30 minutes to 8 hours.

The invention relates in a further embodiment to an aforementioned process, the time period of the treatment according to process step c), i.e. of the first passivation phase, to the time period of the process step according to process step d), i.e. the second passivation phase, being 9:1.

In a further preferred embodiment, the invention relates to an aforementioned process, the temperature of the treatment of the catalyst with the $CO_2$—$N_2$—$O_2$ gas mixture according to step c) and/or step d) being 50 to 70° C.

In a further preferred embodiment, the invention provides an aforementioned process, the $CO_2$ concentration in the $CO_2$—$N_2$—$O_2$ gas mixture during the treatment according to process step c) being 0.5 to 1.5% by vol. In a preferred manner, the invention can provide for the $CO_2$ content of the mixture from step a) for carrying out step c) to be reduced, for example to the aforementioned range.

According to a further preferred embodiment of the present invention, an aforementioned process is made available, the 02 concentration in the $CO_2$—$N_2$—$O_2$ gas mixture during the treatment according to process step c) being 0.25 to 0.8% by vol.

In a further preferred embodiment of the invention, the $O_2$ concentration during the treatment according to process step d) is 5 to 10% by vol.

The invention relates in a further embodiment to an aforementioned process, it being provided that the shaking of the catalyst bed according to process step c) and/or d) is performed at time intervals of 10 to 20 minutes over a period of time of 0.5 to 2 minutes in each case. It is advantageous to set shaking rates of 10 to 50 Hz.

Of course, it is also possible, in particular in the case of pulverulent catalysts and catalysts having very high solidifies, to set the catalyst bed in motion by producing a fluidized layer or by arrangement in a rotary furnace. An important standpoint of the present invention is to agitate the catalyst at least occasionally in the oxygen-carbon dioxide-nitrogen mixture during the passivation phases according to process steps c) and d), for example in an agitated bed.

The stabilization can also be carried out in a particularly preferred manner by stabilizing in a stream of nitrogen having an oxygen content of 0.1 to 1% by vol. and a $CO_2$ content of 0.6% by vol. at temperatures below 80° C.

Of course, it is also possible to carry out the stabilization of the reduced catalyst obtained according to the invention in another manner, for example according to the teaching of U.S. Pat. No. 4,090,980, which is additionally included in the disclosure content of the present application with respect to the process parameters for the stabilization of catalysts.

The invention is illustrated in greater detail with the aid of the following examples:

EXAMPLE 1

According to the Invention 4.5 l of water are introduced into a heatable precipitation container provided with a stirrer and a sodium bicarbonate solution, which was prepared by dissolving 1.5 kg of $NaHCO_3$ in 10 l of water, and a sodium silicate solution (45 g of $SiO_2$=0.75 l of solution) is subsequently added. After this, the mixture is heated to a precipitation temperature of 85° C. with stirring and the addition of a combined metal nitrate solution, which in addition to 400 g of nickel also contained 158 g of $ZrO_2$ and 27 g of $HfO_2$ in the form of the nitrates, is begun. The precipitation time at an average temperature of 80–85° C. was about 2 h. The pH after the precipitation was 8.2–8.5. After termination of the precipitation, the finished suspension was subsequently stirred at 80° C. for about 2 h more. Following this, the suspension is filtered and the filter cake is washed with alkali-free water to an $Na_2O$ content of <0.3 mass %, based on the annealing residue of the product annealed at 800° C. After this, the filter cake is dried at temperatures of 120 to 150° C. for about 14 h and subsequently calcined at 370° C. for 2 h. After the calcination, the intermediate is inertized in a stream of nitrogen (1 000 v/v h), highly heated to 460° C. in a stream of hydrogen (1 000 v/v h) at a heating rate of 5° C./min and reduced at 460° C. for 6 h. It was then inertized at 460° C. in a stream of nitrogen at 1 500 v/v h for 30 minutes, then cooled to 290° C. in a stream of nitrogen (1 500 v/v h), and at this temperature carbon dioxide is added to the nitrogen in such an amount that the $CO_2$ concentration is 2% by vol.

The catalyst is treated at 280° C. with this mixture for 30 minutes, subsequently cooled to 50° C. in the same gas mixture and stabilized at temperatures below 80° C. in a stream of nitrogen (1 500 v/v h) having an oxygen content of 0.1 to 1% by vol. and a $CO_2$ content of 0.6% by vol. The oxygen concentration was chosen such that the catalyst temperature did not exceed 80° C. The stabilization time at temperatures of <80° C. was 5 h.

The reduced and stabilized catalyst contains about 50 mass % of nickel, 20 mass % of $ZrO_2$, 5 mass % of $SiO_2$ and 3 mass % of $HfO_2$. The XRD investigations showed a monomodal nickel crystallite size distribution with a maximum of 42 angstroms. After a one-hour afterreduction, the degree of reduction of the catalyst at 100° C. is 78% (loading in a stream of hydrogen: 1 000 v/v h). The phase analysis of the dried filter cake showed the presence of the sepiolite-like structure: $Ni_4Zr_6O_{15}(OH)_2$ (with partial replacement of the OH ions by carbonate ions).

EXAMPLE 2

According to the Invention 4.5 l of water are introduced into the heatable precipitation container and a metal nitrate solution which in addition to 400 g of nickel also contains zirconium and hafnium in the form of a nitrate solution is subsequently added. The molar ratio of nickel to $ZrO_2$ in the metal nitrate solution is about 2, the molar ratio of $ZrO_2$ to $HfO_2$ about 25. After the addition of the metal nitrate solution, the mixture is heated with stirring to a temperature of 60° C. and subsequently precipitated using an aqueous sodium carbonate solution (150 g of sodium carbonate/l of solution) to a final pH of about 8.5. The precipitation time was likewise about 2 h. After termination of the precipitation, the mixture was subsequently stirred at temperatures of 60–70° C., then filtered and processed further as described in example 1.

The finished catalyst contains about 40 mass % of nickel, 40 mass % of $ZrO_2$ and 3 mass % of $HfO_2$. The monomodal Ni crystallite size distribution has a maximum at 38 angstroms. The degree of reduction of the catalyst after a one-hour afterreduction at 100° C. is 80%. The phase analysis of the dried filter cake showed a mixture of nickel hydroxynitrate ($Ni_3(OH)_4(NO_3)_2$) and nickel hydroxycarbonate ($Ni_2(OH)_2CO_3 4H_2O$).

EXAMPLE 3

Comparison Example 305.76 g of Ni ($NO_3$) $6H_2O$ and 29.52 g of Al ($NO_3$)$_3$ $9H_2O$ are dissolved in 1 760 ml of distilled water and 2.32 g of zirconium carbonate in 9 ml of $HNO_3$ (56 mass %). Both solutions are combined and heated to 101° C. This mixed salt solution is added uniformly in the course of 3 minutes to a hot intensively stirred sodium carbonate solution at 100° C., which has been prepared from 147.04 g of $Na_2CO_3$ and 1 416 ml of distilled water. 27.76 g of kieselguhr are stirred into the freshly precipitated suspension and the mixture formed in the course of this is stirred for a further 3 minutes. The precipitation product is then filtered and washed with hot water at 70° C. until the alkali content of the wash water is about 20 mg of $Na_2O$/l. The filter cake obtained in this manner is suspended in hot water at 70° C. (quantitative ratio of filter cake to water=1:1), stirred for 60 minutes and then filtered again. The filter cake then obtained is filtered again. The filter cake formed here is extruded to give cylindrical shaped articles (diameter 5 mm, length 8 to 10 mm) and subsequently dried at increasing temperature (50 to 60° C.) with air to a residual content of water of <10 mass %, based on dried mass. The dried material is highly heated to 470° C. in a stream of hydrogen after prior inertization in a stream of nitrogen (1 000 v/v h, 30 min) with a loading of 400 v/v h and a heating time of 5° C./min and reduced at this temperature over a period of time of 4 h. The phases takovite (carbonate variant) and nickel hydroxysilicate with carbonate incorporation were detected in the dried intermediate. Stabilization was performed as in the examples according to the invention. The properties of the catalyst are compared to those of the catalysts according to the invention in the table.

EXAMPLE 4

Comparison Example 2.7 kg of sodium carbonate were suspended in 6 l of water and warmed to 60° C. In the course of 30 minutes, 6.6 l of a solution of sodium silicate having a content of 15 g of $SiO_2$/l and subsequently 3 l of a nickel nitrate solution having a content of 150 g of Ni/l of solution were added with vigorous stirring in the course of 2 h. The precipitation suspension was then stirred at 60° C. for 1 h. After this, a further 3.5 l of a nickel nitrate solution having a content of 150 g of Ni/l of solution were introduced into the precipitation suspension in the course of 2 h. The precipitate was filtered off and washed with water. The filter cake was subsequently dried at 130° C. for 10 h, reduced at 450° C. in a stream of hydrogen after prior calcination and inertization, as described in example 1, for 6 h, and stabilized at temperatures of <80° C. after inertization in a stream of nitrogen (1 000 v/v h, 30 min at 450° C.) and after cooling in a stream of nitrogen using a stream of nitrogen containing 0.1 1 % of $O_2$ (1 500 v/v h). The stabilization time was 8 h. The reduced and stabilized catalyst contains about 62% of nickel and 20% of $SiO_2$. The degree of reduction of the catalyst after a one-hour afterreduction at 100° C. is 75%.

The phase analysis of the dried filter cake mainly showed nickel hydroxysilicate with carbonate incorporation.

The catalytic characterization of the catalysts was performed under the following conditions:

A) Hydrogenation of glucose in a 0.5 l stirred autoclave with measurement of hydrogen consumption at constant pressure:

| Amount of catalyst: | 1.2 g |
|---|---|
| Reaction mixture: | 120 g of glucose and 90 g of water |
| Reaction pressure: | 125 bar |
| Reaction temperature: | 135° C. |
| Stirrer speed: | 2 000 revolutions/minute |

The time in which 98.5% of the glucose was hydrogenated was used as a measure of the hydrogenation activity.

B) Hydrogenation of nitrobenzene to aniline in a 0.5 l autoclave with measurement of hydrogen consumption at constant pressure:

| Amount of catalyst: | 0.25 g |
|---|---|
| Reaction mixture: | 80 g, 40 g of water |
| Reaction pressure: | 25 bar |
| Reaction temperature: | 120° C. |
| Stirrer speed: | 2 000 revolutions/minute |

The time in which 100% of the nitrobenzene was reacted was used as a measure of the hydrogenation activity.

The stability of the catalysts was characterized by the increase in the average Ni crystallite size which arises in the reaction mixture after the hydrogenation reaction under the pressure and temperature conditions of the hydrogenation after a 100-hour treatment.

The XDR wide-angle investigations for qualitative phase assignment were carried out under the following experimental recording conditions on a measuring station from Rich. Seifert & CO Freiberger Prazisionsmechanik GmbH:

| Generator data: | 34 kv/30 mA |
|---|---|
| Goniometer: | HZG4 |
| Radiation: | Cu—$K_8$ |
| Filter: | curved graphite monochromator |
| Angular range: | 2 = 10°–70° |
| Step width: | Δ = 0.05° |
| Count time: | 4s |

The processing of the data was carried out in the analysis file APX63 (SEIFERT FPM). The JCPDS analysis file 1997 was used for the assignment of the crystalline structures.

The mean primary particle size of the nickel was likewise determined using a measuring station from Rich. Seifert & CO Freiberger-Präzisionsmechanik GmbH, the scattering curve sections having been recorded perpendicularly to the (111) lattice plane from the interference line spreading under the following conditions:

| Generator data: | 40 kv/30 mA |
|---|---|
| Goniometer: | XDR7 |
| Radiation: | Cu—$K_6$ |
| Filter: | Ni |
| Angular range: | 2 = 41°–49° |
| Step width: | Δ - 0.050 |
| Count time: | 20s |

Conclusions on the modality (mono gaus line profile or bimodal gaus line profile) of the Ni-(111) line profile were obtained by use of the peak resolution program PF4 from Jandel Corporation.

The characterization of the catalysts is clear from the following table:

| Catalyst | Hydrogenation time for nitrobenzene in min (conversion: 100%) | Aniline yield in % | Hydrogenation time for glucose in min (conversion: 98.5%) | Mean Ni crystallite size in angstroms (before the reaction) | Mean Ni crystallite size in angstroms (after the stability test |
|---|---|---|---|---|---|
| Example 1 | 97 | 99.2 | 41 | 48 | 61 |
| Example 2 | 95 | 99.1 | 43 | 56 | 66 |
| Example 3 comparison example | 129 | 98.6 | 52 | 107 | 134 |
| Example 4 comparison example | 115 | 98.7 | 50 | 72 | 107 |

The results show the advantages of the catalysts according to the invention, which lie in their high catalytic activity and high stability, as the small increase in the Ni crystallite sizes confirms.

What is claimed is:

1. A catalyst, useful for the hydrogenation of functional groups of organic compounds in the presence of water, comprising nickel on a support which is $ZrO_2$, $ZrO_2HfO_2$, $SiO_2 \cdot ZrO_2$, $SiO_2 \cdot ZrO_2HfO_2$ or a mixture thereof, the catalyst being stabilized, containing nickel crystallites having a monomodal nickel crystallite size distribution, a nickel content of 25 to 60 mass % based on the total mass of the catalyst, a $ZrO_2$ content of from 20 to 75 mass % based on the total mass of the catalyst and a degree of reduction of at least 65%.

2. The catalyst as claimed in claim 1, wherein the maximum of the nickel crystallite size distribution is 25 to 90 angstroms.

3. The catalyst as claimed in claim 1, wherein the support is a mixture of two or three of the $ZrO_2$, $ZrO_2HfO_2$, $SiO_2 \cdot ZrO_2$, and $SiO_2 \cdot ZrO_2HfO_2$.

4. The catalyst as claimed in claim 1, wherein the support contains $SiO_2$ and the $SiO_2$ content does not exceed 40 mass % based on the total mass of the catalyst.

5. The catalyst as claimed in claim 1, wherein the support contains $HfO_2$ and the $HfO_2$ content does not exceed 7.5 mass % based on the total mass of the catalyst.

6. The catalyst as claimed in claim 1, wherein the catalyst is in the form of a powder having particle sizes of 1 to 100 $\mu$m.

7. The catalyst as claimed in claim 6, wherein the catalyst particle sizes is 2 to 30 $\mu$m.

8. A process for the preparation of a nickel-containing supported catalyst, useful for the hydrogenation of functional groups of organic compounds in the presence of water, comprising nickel on a zirconium-containing support, the catalyst being stabilized, containing nickel crystallites having a monomodal nickel crystallite size distribution, a nickel content of 25 to 60 mass % based on the total mass of the catalyst, a $ZrO_2$ content of 20 to 75 mass % based on the total mass of the catalyst and a degree of reduction of at least 65%, the process comprising causing a precipitation product to form by combining an $Ni^{2+}$- and $Zi^{4+}$-containing solution with a basic solution up to a final pH of 8 to 9, calcining the precipitation product at temperatures from 300° C. to 650° C., reducing the calcined precipitation with hydrogen at temperatures from 250° C. to 550° C. and stabilizing the reduced product.

9. The process as claimed in claim 8, wherein the precipitation product is rendered inert after calcination and before reduction.

10. The process as claimed in claim 8, wherein the basic solution is a solution of NaOH, $NaHCO_3$, $Na_2CO_3$ or a mixture of two or more of these substances.

11. The process as claimed in claim 8, wherein the $Ni^{2+}$- and $Zr^{+4}$-containing solution contains at least one of nitrate and $Hf^{4+}$.

12. The process as claimed in claim 8, wherein the $Ni^{2+}$- and $Zr^{4+}$-containing solution contains $SiO_2$.

13. The process as claimed in claim 8, wherein the precipitation is effected at a temperature from 65° C. to 95° C.

14. The process as claim 8, wherein the precipitation product is filtered after the precipitation, washed, and subsequently dried in a nonreducing atmosphere to obtain a precursor catalyst.

15. A process as claimed in claim 14, wherein the preparation of the precursor catalyst results in the formation of at least one nickel hydroxynitrate ($Ni_3(OH)_4(NO_3)_2$) or nickel hydroxynitrate-$(Ni_3(OH)_4(NO_3)_2$ containing phase.

16. The process as claimed in claim 14, wherein the catalyst precursor is shaped before calcination into tablets, extrudates, cushion-shaped articles or spheres.

17. The process as claimed in claim 14, wherein the catalyst precursor is shaped after calcination to give tablets, extrudates, cushion-shaped articles or spheres.

18. The process as claimed in claim 8, wherein the gas loading during the reduction is 500 to 3,000 v/v h.

19. The process as claimed in claim 8, wherein the catalyst is stabilized by contact with an $O_2$—$N_2$—$CO_2$ mixture.

20. The process as claimed in claim 8, wherein the stabilization is effected at a temperature below 80° C.

* * * * *